United States Patent
Strohm et al.

(10) Patent No.: US 10,365,252 B2
(45) Date of Patent: Jul. 30, 2019

(54) METHOD AND APPARATUS FOR SENSING A SAMPLE

(71) Applicants: Eric M. Strohm, Mississauga (CA); Michael J. Moore, Kitchener (CA); Michael C. Kolios, Toronto (CA)

(72) Inventors: Eric M. Strohm, Mississauga (CA); Michael J. Moore, Kitchener (CA); Michael C. Kolios, Toronto (CA)

(*) Notice: Subject to any disclaimer, the term of this patent is extended or adjusted under 35 U.S.C. 154(b) by 86 days.

(21) Appl. No.: 15/430,719

(22) Filed: Feb. 13, 2017

(65) Prior Publication Data
US 2018/0231505 A1 Aug. 16, 2018

(51) Int. Cl.
*G01N 29/24* (2006.01)
*G01N 21/17* (2006.01)

(52) U.S. Cl.
CPC ..... *G01N 29/2418* (2013.01); *G01N 21/1702* (2013.01)

(58) Field of Classification Search
CPC .................. G01N 29/2418; G01N 2291/048
USPC .......................................................... 73/655
See application file for complete search history.

(56) References Cited

U.S. PATENT DOCUMENTS

| 5,025,665 A | * | 6/1991 | Keyes, IV | G01N 29/07 73/159 |
| 2010/0037695 A1 | * | 2/2010 | Tsujita | A61B 5/0073 73/587 |

* cited by examiner

*Primary Examiner* — Tarun Sinha
(74) *Attorney, Agent, or Firm* — Perry + Currier Inc.

(57) ABSTRACT

There is provided a method for sensing a sample. The method includes the following steps: first a light beam is directed onto the sample. The sample transmits at least a portion of the light beam to form a transmitted light beam. Next, the transmitted light beam is received at an acoustic transducer. The acoustic transducer absorbs at least a portion of the transmitted light beam and in response generated an acoustic wave. Subsequently, an electrical signal is generated at the acoustic transducer. The electrical signal is generated based on at least a portion of the acoustic wave.

20 Claims, 11 Drawing Sheets

METHOD AND APPARATUS FOR SENSING A SAMPLE

FIELD

The present specification relates to a method and apparatus for sensing a sample, and in particular to a method and apparatus for sensing a sample based on optical attenuation.

BACKGROUND

Systems and methods for sensing and/or imaging samples can rely on a number of different techniques including relying on a probe light beam to interrogate the sample. Beams of different wavelengths interact differently with different samples. As a result, for a given sensing technique that relies on a given interaction between the probe beam and the sample, the appropriate wavelength should be chosen to produce the given interaction. For example, if a sensing technique relies on measuring the portion of the probe light beam that is transmitted through the sample, then the wavelength of the probe light beam can be chosen such that the sample at least partially transmits the probe light beam.

Moreover, different wavelengths can interact with different features and/or portions of the sample and yield different sensing information. In addition, in some applications the probe light beam can be chosen to be non-destructive to the sample. As such, a large variety of sensing techniques are needed to provide adequate sensing options for sensing the various properties of different types of samples.

In addition to using an optical probe beam, acoustic waves can also be used to sense a sample. However, acoustic waves can require a coupling medium disposed between the sample and the sensor, to allow for adequate transmission of acoustic waves between the sample and the sensor. These coupling mediums are often liquids. However, some samples need to be maintained in a dry state and cannot be used in conjunction with a liquid coupling medium.

SUMMARY

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, ZZ, and the like). Similar logic can be applied for two or more items in any occurrence of "at least one . . . " and "one or more . . . " language.

An aspect of the present specification provides a method for sensing a sample, the method comprising: directing a light beam onto the sample, the sample transmitting at least a portion of the light beam to form a transmitted light beam; receiving the transmitted light beam at an acoustic transducer, the acoustic transducer absorbing at least a portion of the transmitted light beam and in response generating an acoustic wave; and generating an electrical signal at the acoustic transducer, the electrical signal generated based on at least a portion of the acoustic wave.

The sample can be separated from the acoustic transducer by an acoustic gap.

The acoustic gap can be an air gap.

The acoustic transducer can generate the acoustic wave based on the photoacoustic effect.

The acoustic transducer can comprise an ultrasound transducer.

The ultrasound transducer can have a central frequency in a range of about 100 MHz to about 1000 MHz.

The acoustic transducer can comprise: a buffer member configured to conduct the acoustic wave; and a piezoelectric element acoustically coupled to the buffer member, the piezoelectric element configured to generate the electrical signal based on the acoustic wave.

The light beam can comprise a pulsed laser beam.

The light beam can be focused at one of: a first point underneath a surface of the sample, the first point being inside the sample; and a second point at the surface of the sample.

The method can further comprise: after the receiving the transmitted light beam at the acoustic transducer, receiving at the acoustic transducer at least a portion of a further acoustic wave, the further acoustic wave generated by the sample absorbing at least a further portion of the light beam and in response generating the further acoustic wave; and generating a further electrical signal at the acoustic transducer, the further electrical signal generated based on at least a portion of the further acoustic wave.

The sample can generate the further acoustic wave based on the photoacoustic effect.

The method can further comprise: recording the electrical signal and the further electrical signal respectively as a first portion and a second portion of a continuous time-domain electrical signal, the first portion ending no later than a start of the second portion.

The method can further comprise: directing a probe acoustic wave onto the sample, the probe acoustic wave generated at the acoustic transducer; receiving at the acoustic transducer an echo acoustic wave, the echo acoustic wave generated at least partially by the sample in response to the probe acoustic wave; and generating an additional electrical signal at the acoustic transducer, the additional electrical signal generated based on at least a portion of the echo acoustic wave.

The method can further comprise: recording the electrical signal, the further electrical signal, and the additional electrical signal respectively as a first portion, a second portion, and a third portion of a continuous time-domain electrical signal, the first portion ending no later than a start of the second portion, and the second portion ending no later than a corresponding start of the third portion.

A further aspect of the present specification provides a method of forming an image of a sample, the image having a plurality of pixels, the method comprising: for each given pixel of the image: directing a light beam onto a given area of the sample, the given area corresponding to the given pixel, the given area of the sample transmitting at least a portion of the light beam to form a transmitted light beam; receiving the transmitted light beam at an acoustic transducer, the acoustic transducer absorbing at least a portion of the transmitted light beam and in response generating an acoustic wave; generating an electrical signal at the acoustic transducer, the electrical signal generated based on at least a portion of the acoustic wave; and determining a visual characteristic of the given pixel based on a corresponding characteristic of the electrical signal.

The visual characteristic can comprise a grey scale intensity and the corresponding characteristic of the electrical signal can comprise an amplitude of the electrical signal.

The sample can be separated from the acoustic transducer by an acoustic gap.

The acoustic gap can be an air gap.

A yet further aspect of the present specification provides an apparatus for sensing a sample, the apparatus comprising: an optical outlet configured to direct a light beam onto the sample, at least a portion of the light beam being transmittable through the sample to form a transmitted light beam; an acoustic transducer positioned to receive the transmitted light beam, the acoustic transducer configured to: absorb at least a portion of the transmitted light beam and in response generate an acoustic wave; and generate an electrical signal based on at least a portion of the acoustic wave; and a sample holder disposed between the optical outlet and the acoustic transducer, the sample holder configured to support the sample in a path of the light beam.

The acoustic transducer can comprise: a buffer member proximate the sample holder, the buffer member configured to conduct the acoustic wave; and a piezoelectric element distal from the sample holder, the piezoelectric element acoustically coupled to the buffer member, the piezoelectric element configured to generate the electrical signal based on the acoustic wave.

The optical outlet can comprise a lens having an optical focal point; the buffer member can be shaped to have an acoustic focal point; and the lens and the buffer member can be positioned such that the optical focal point about coincides with the acoustic focal point.

The acoustic transducer can comprise an ultrasound transducer having a central frequency in a range of about 100 MHz to about 1000 MHz.

DESCRIPTION OF THE DRAWINGS

Some implementations of the present specification will now be described, by way of example only, with reference to the attached Figures, wherein.

DETAILED DESCRIPTION

Figure 1:
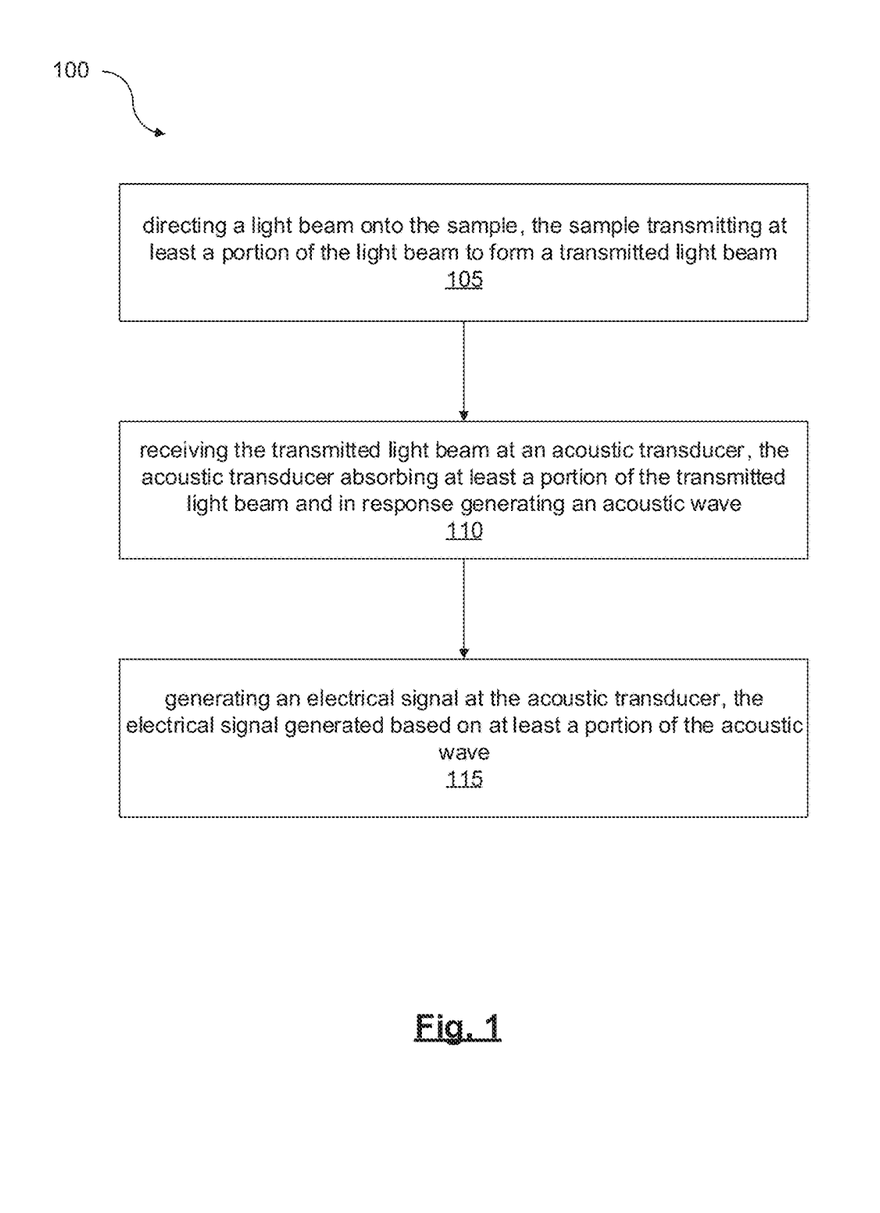
FIG. 1 depicts a flow chart showing the steps of a method for sensing a sample, according to non-limiting implementations.

FIG. 1 depicts a flow chart showing the steps in an exemplary method 100 for sensing a sample. At step 105, a light beam is directed onto the sample, which sample in turn transmits at least a portion of the light beam to form a transmitted light beam. As the sample transmits the light beam, the light beam can become attenuated by the sample. Such attenuation can comprise, but is not limited to, the light beam becoming at least partially absorbed, scattered, and/or refracted by the sample.

Next, at step 110, the transmitted light beam is received at an acoustic transducer, which is configured to absorb at least a portion of the transmitted light beam and in response generate an acoustic wave. The generation of this acoustic wave can be based on the photoacoustic effect, according to which light and/or electromagnetic radiation is absorbed by an object, which object in response generates acoustic waves.

Next, at step 115, the acoustic transducer generates an electrical signal based on at least a portion of the acoustic wave. This electrical signal can provide a measure of the optical attenuation of the light beam by the sample, and as such can be used as a method of sensing some properties of the sample contributing to the attenuation. This method and/or mode of sensing the sample can be described as optical attenuation sensing or as transmission photoacoustic (tPA) sensing.

Unlike other sensing methods that rely on acoustic waves, method 100 does not rely on the transmission of acoustic waves from the sample to the acoustic transducer because the information about the sample is transmitted to the acoustic transducer by the transmitted light beam. As such, method 100 does not require a coupling medium to fill any space or gap between the sample and the acoustic transducer to allow for adequate transmission of acoustic waves from the sample to the acoustic transducer. In other words, in some implementations there can be an acoustic gap separating the sample from the acoustic transducer. In some implementations, this acoustic gap can be an air gap. In other implementations, the acoustic gap can be filled with one or more gases including, but are not limited to, nitrogen gas, noble gases, and the like.

The acoustic gap can represent an absence of a coupling medium that would allow for adequate transmission of acoustic waves from the sample to the acoustic transducer to allow for sensing of those waves by the transducer. Adequate transmission of acoustic waves can depend on a number of factors, including but not limited to, the acoustic impedance mismatch between the sample and the coupling medium. For example, and without limitation, if the mismatch is about 100× or more, such an impedance mismatch would result in only about 3-4% acoustic transmission at the interface between the sample and the coupling medium (disposed between the sample and the acoustic transducer). For a coupling medium such as air, the acoustic impedance mismatch can be much larger, and the acoustic transmission from the sample, through the air gap, and towards the acoustic transducer can be very small and approaching non-detectable levels.

In addition to acoustic impedance mismatch, adequate transmission of acoustic waves can also depend on the acoustic attenuation of and/or in the coupling medium. This acoustic attenuation can also depend on the frequency of the acoustic waves being transmitted through the coupling medium. In some implementations, in the frequency range of about 100 MHz to about 1000 MHz, acoustic attenuation greater than about 30-40 dB can result in a level of acoustic transmission that would be inadequate for and/or present challenges to the practical or reliable sensing/measurement of those acoustic waves by the acoustic transducer.

Given the impact of acoustic impedance mismatch and attenuation on the transmission of acoustic waves from the sample to the acoustic transducer, the acoustic gap can comprise a physical space and/or gap separating the sample from the acoustic transducer, which space or gap is filled with a coupling medium that has an acoustic impedance mismatch with the sample of at least about 100× and/or an acoustic attenuation, in the frequency range of about 100 MHz to about 1000 MHz, greater than about 30 dB. In some implementations, the acoustic gap can comprise a physical space and/or gap separating the sample from the acoustic transducer, which space or gap is filled with a coupling medium that has an acoustic impedance mismatch with the sample of at least about 100× and/or an acoustic attenuation, in the frequency range of about 100 MHz to about 1000 MHz, greater than about 40 dB.

While the above description discusses the space or gap being "filled" with a coupling medium, it is also contemplated that the acoustic gap can comprise a space that is at least partially evacuated and/or an at least partial vacuum that has acoustic impedance mismatch and/or causes acoustic attenuation similar to those discussed above.

The acoustic transducer can comprise a device that is configured to interconvert between acoustic and electrical energy. While the description herein refers to "acoustic waves", it is contemplated that "acoustic waves" can generally comprise various types of pressure waves. The acoustic transducer can comprise an ultrasound transducer. In some implementations, the acoustic transducer can comprise an ultra-high frequency ultrasound transducer. Moreover, in some implementations, the acoustic transducer can comprise an ultrasound transducer having a central frequency in a range of about 100 MHz to about 1000 MHz.

The sample can comprise a variety of different materials including, but not limited to, biological materials such as cells, tissue samples, and the like, and inorganic samples such as semiconductors, integrated circuits, and the like. The light beam can comprise any wavelength or range of wavelengths that are at least partially transmittable by the sample. For example, the light beam can comprise visible, near infra-red, infra-red (IR), and other suitable wavelengths and/or wavelength ranges. In some implementations, the light beam can comprise a laser. Moreover, in some implementations, the light beam can be pulsed. In some implementations, the light beam can comprise a laser beam with a wavelength of about 532 nm, a pulse repetition frequency of about 4 kHz, and a pulse width of about 330 ps.

Figure 2:
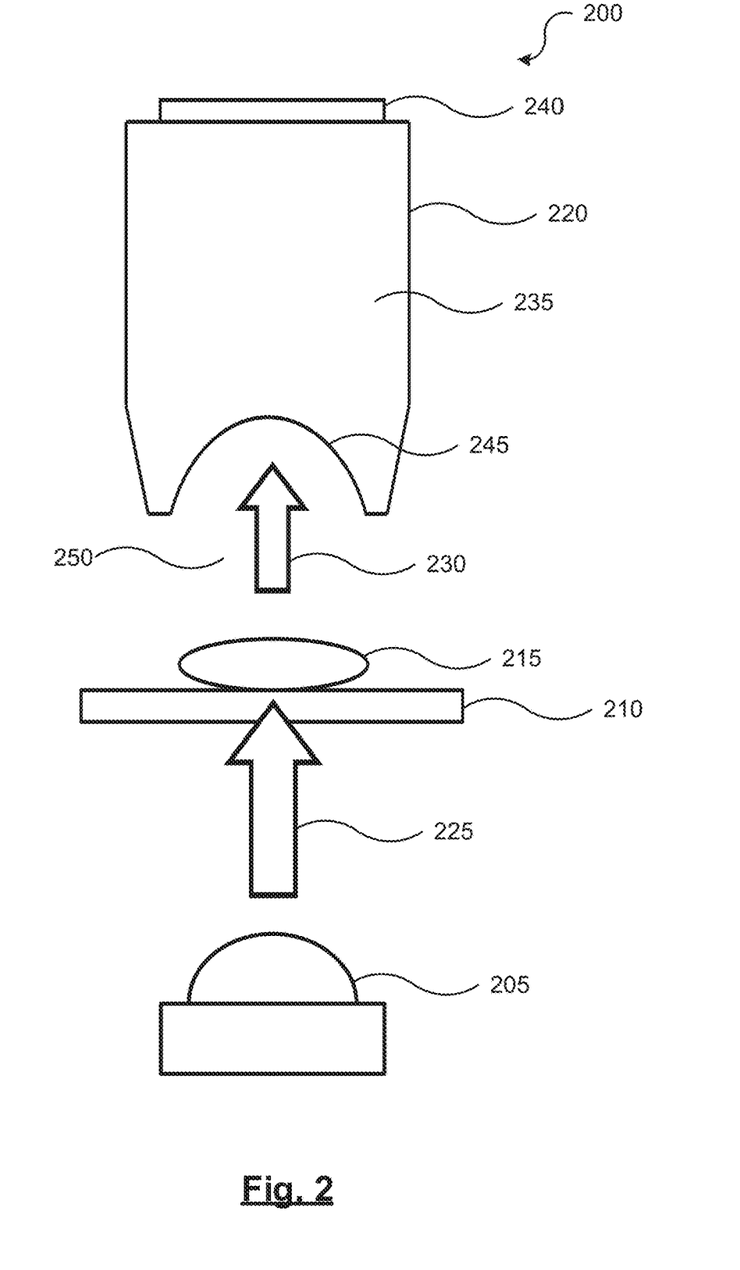
FIG. 2 depicts a cross-sectional schematic representation of an apparatus for sensing a sample, according to non-limiting implementations.

Referring now to FIG. 2, a cross-sectional schematic representation of an apparatus 200 for sensing a sample is shown. Method 100 can be implemented using apparatus 200. It is also contemplated that method 100, and any other methods described herein for sensing a sample, need not be limited to being implemented using apparatus 200, and that these methods can be implemented using other suitable apparatuses.

Apparatus 200 comprises an optical outlet 205, an acoustic transducer 220, and a sample holder 210 disposed between optical outlet 205 and acoustic transducer 220. Optical outlet 205 directs a light beam 225 towards a sample 215 resting on and/or supported by sample holder 210 in the path of light beam 225. Light beam 225, in turn, is chosen to be at least partially transmittable through sample 215 to form a transmitted light beam 230.

Transmitted light beam 230, in turn, propagates from sample 215 towards acoustic transducer 220, which is positioned to receive transmitted light beam 230. Acoustic transducer 220 is configured to absorb at least a portion of transmitted light beam 230 and in response generate an acoustic wave (not shown in FIG. 1). Moreover, acoustic transducer 220 is further configured to generate an electrical signal based on at least a portion of this acoustic wave. As such, this electrical signal can provide a measure of the optical attenuation of light beam 225 by sample 215.

Apparatus 200 can comprise an acoustic gap 250 separating sample 215 from acoustic transducer 220. Acoustic gap 250 can be an air gap, or filled with one or more other gases. Optical outlet 205 can comprise any suitable component for directing light beam 225 onto sample 215, including but not limited to, a lens, a microscope objective les, a mirror, an integration rod, a fiber optic, a light emitting diode, and the like.

Sample holder 210 can comprise any suitable structure and/or material that can hold sample 215 in the path of light beam 225, and also transmit at least a portion of light beam 225 to interact with sample 215. In some implementations, sample holder 210 can comprise a glass slide. In other implementations (not shown in the Figs.), sample holder 210 can define an aperture, opening, and/or space for light beam 225 to pass through and impinge directly onto sample 215 without having to first pass through and/or interact with sample holder 210.

Acoustic transducer 220 can comprise a buffer member 235 and a piezoelectric element 240 acoustically coupled to buffer member 235. As shown in FIG. 2, acoustic transducer can be configured and/or oriented such that buffer member 235 is proximate sample holder 210 and piezoelectric element 240 is distal from sample holder 210. Buffer member 235 can be configured to conduct the acoustic waves to and from piezoelectric element 240. In some implementations, buffer member 235 can comprise a sapphire buffer rod.

While the acoustic transducers depicted and described herein include a buffer member, it is contemplated that in some implementations the acoustic transducer may not comprise a buffer member or may comprise a buffer member that comprises materials or has a shape that is different than the buffer members described herein.

Piezoelectric element 240 can receive acoustic waves and in response generate an electrical signal based on those acoustic waves. In this mode, piezoelectric element 240 can be used to measure and/or sense acoustic waves. In addition, piezoelectric element 240 can also be powered by an electrical signal to generate acoustic waves, which then travel through buffer member 235 towards sample holder 210. In this second mode, piezoelectric element 240 can be used to emit acoustic waves that can be used to probe sample 215, and will be discussed in greater detail below.

In some implementations, piezoelectric element 240 can comprise a piezoelectric layer of zinc oxide, which can be epitaxially grown between two gold electrodes on buffer member 235. In some implementations, the buffer member can comprise a buffer rod. Moreover, in some implementations, buffer member 235 can comprise a depression 245 ground into buffer member 235. This depression 245 can act as an acoustic lens, and can have any suitable shape including, but not limited to, hemispherical, parabolic, and the like.

In implementations where acoustic transducer 220 generates acoustic waves to be used for probing sample 215 (such implementations are discussed below), plane acoustic waves generated by piezoelectric element 240 can propagate through buffer member 235 and can be focused to convergent acoustic waves by depression 245 ground into buffer member 235. When depression 245 is hemispherical in shape, the plane acoustic waves can be focused by depression 245 into convergent spherical waves. As such, acoustic transducer 220 can have an acoustic focal point that is located outside of acoustic transducer 220 and spaced from acoustic transducer 220 in the direction towards sample holder 210.

In some implementations, optical outlet 205 can comprise a lens having an optical focal point outside of optical outlet 205 and spaced from optical outlet 205 in the direction of sample holder 210. In some implementations, the lens of optical outlet 205 and buffer member 235 of acoustic transducer 220 can be positioned relative to one another such that the optical focal point of optical outlet 205 about coincides with the acoustic focal point of buffer member 235. In some implementations, these about coincident focal points are one or more of at the surface of sample 215 or beneath the surface of and inside sample 215. In some implementations, optical outlet 205 and acoustic transducer 220 can be aligned coaxially on opposite sides of sample holder 210.

Figure 3:
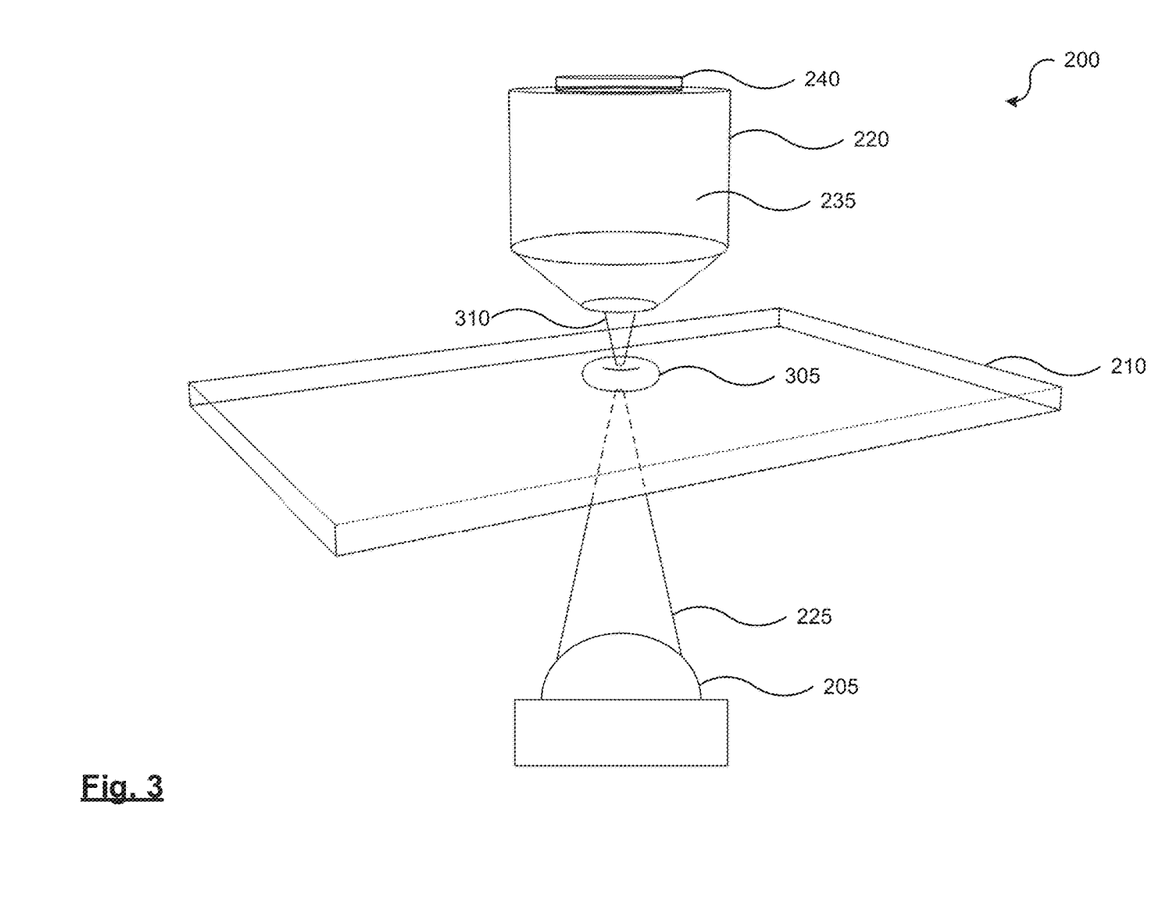
FIG. 3 depicts a top perspective view of the apparatus shown in FIG. 2.

Turning now to FIG. 3, a top perspective view of apparatus 200 is shown. Light beams 225 are shown as being convergent at an optical focal point at a sample 305. It is contemplated that the focal point can be at the surface of sample 305, which would facilitate sensing the surface of sample 305. In addition, the position of sample 305 relative to the focal point can be changed and/or different such that the focal point is positioned underneath the surface of sample 305 and/or inside sample 305. At least a portion of light beam 225 is transmitted through sample 305 to form a transmitted light beam 310. Transmitted light beam 310, in turn, propagates towards acoustic transducer 220.

While sample holder 210 is shown as being larger in FIG. 3 than in FIG. 2, the depiction of apparatus 200 in FIG. 2 is schematic and the various components are not necessarily drawn to scale. Moreover, the size and/or shape of the sample holder is not intended to be limiting, and it is contemplated that sample holders of various suitable shapes and sizes can be used.

Figure 4:
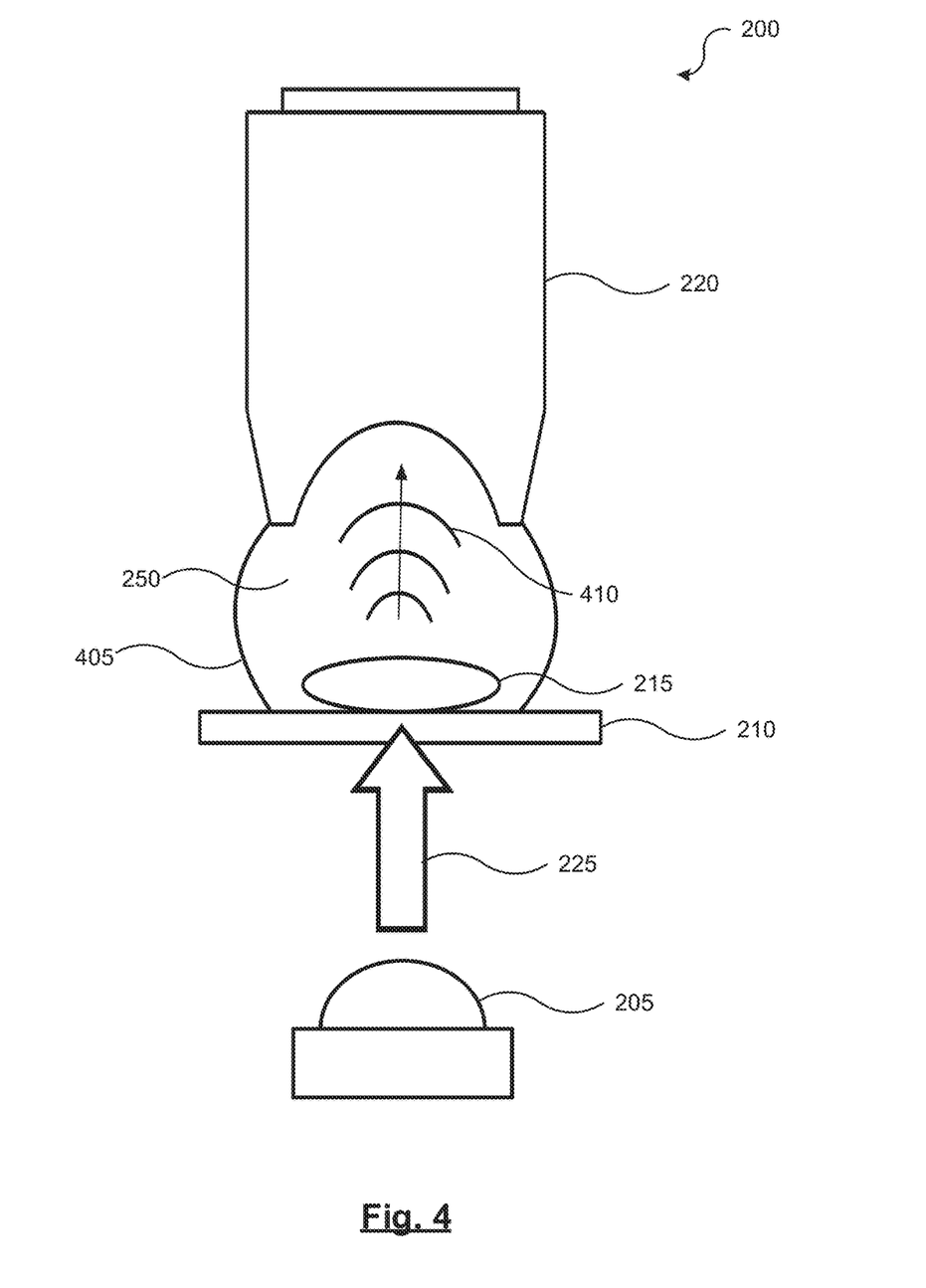
FIG. 4 depicts a cross-sectional schematic representation of the apparatus shown in FIG. 2 in an alternate sensing mode.

FIG. 4 shows a cross-sectional schematic representation of apparatus 200. FIG. 4 is similar to FIG. 2, with the main difference being that in FIG. 4 an acoustic coupling medium 405 fills at least a portion of acoustic gap 250 to allow for adequate transmission of acoustic waves 410 from sample 215 to acoustic transducer 220. Coupling medium 405 can comprise water, aqueous solutions, oils, and other liquids, pastes, gels, and the like.

Use of coupling medium 405 can allow apparatus 200 to be used in an additional sensing mode. When sample 215 is exposed to light beam 225, sample 215 can absorb a portion of light beam 225 and in response generate acoustic waves 410. Acoustic waves 410 can be generated based on the photoacoustic effect. Acoustic waves 410 can then travel through coupling medium 405 towards acoustic transducer 220. Acoustic transducer 220, in turn, can receive acoustic waves 410 and generate a further electrical signal based on at least a portion of acoustic waves 410. As such, this further electrical signal can be a measure of the absorption of light beam 225 by sample 215. This additional mode of sensing sample 215 can be described as photoacoustic (PA) sensing.

In implementations where coupling medium 405 is compatible with the transmission of the transmitted light beam from sample 215 to acoustic transducer 220, apparatus 200 as shown in FIG. 4 can be used in a dual sensing mode where apparatus 200 can be used for both photoacoustic and optical attenuation sensing using the same pulse and/or illumination period of light beam 225. In this dual sensing mode, a given illumination period of light beam 225 forms transmitted light beam 230 (shown in FIG. 2) which travels at the speed of light (in the coupling medium) towards acoustic transducer 220. The same given illumination period also forms acoustic waves 410 (shown in FIG. 4) which travel at the speed of sound (in the coupling medium) towards acoustic transducer 220.

Figure 5:
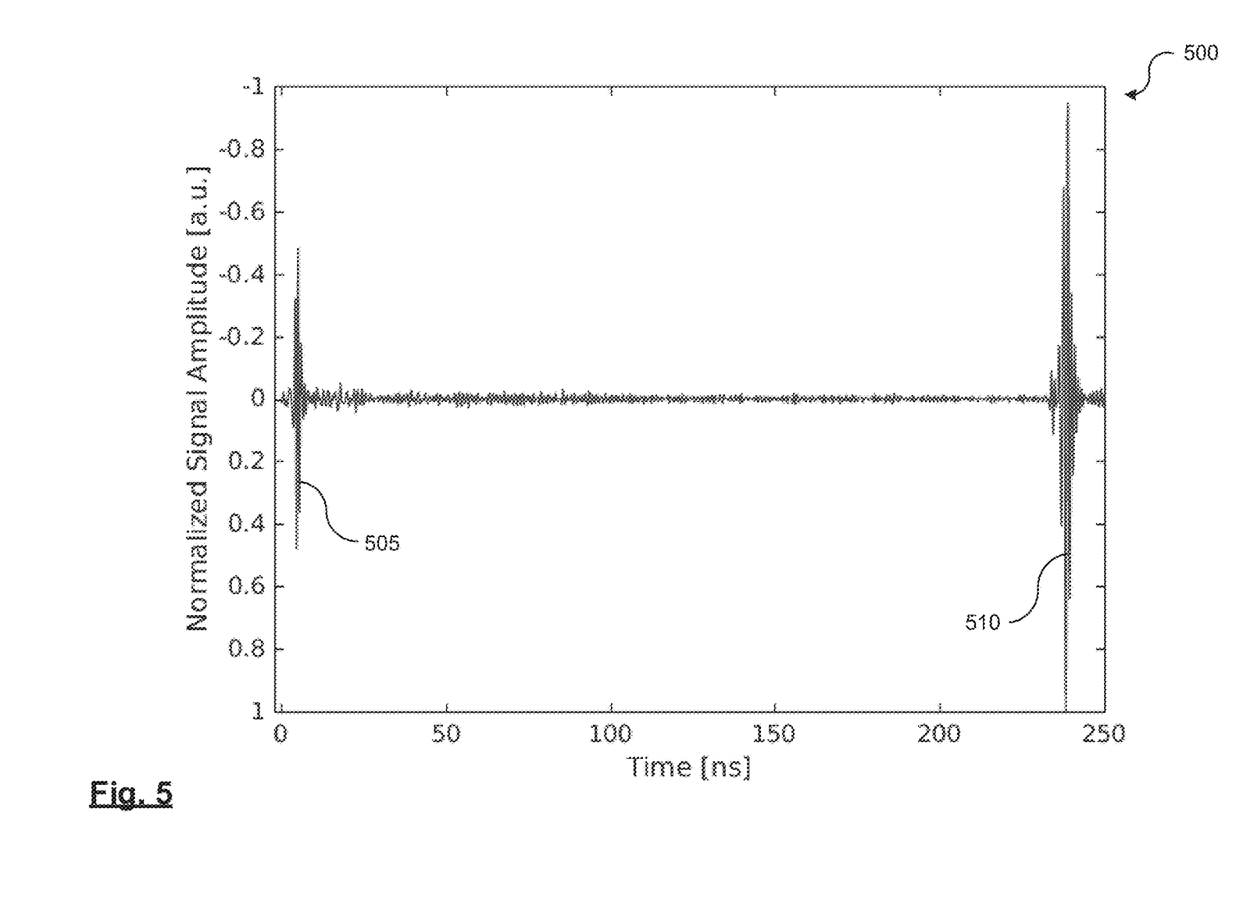
FIG. 5 depicts a plot of electrical signal amplitude over time.

As light travels much faster than sound, the electrical signal generated in response to transmitted light beam 230 is sensed/measured earlier than the electrical signal generated in response to acoustic wave 410. In some implementations, the electrical signal output from acoustic transducer 220 can be recorded as a first (earlier) portion and a second (later) portion of a continuous time-domain electrical signal. In some implementations, the first, earlier portion can end no later than the start of the second, later portion. FIG. 5 shows a plot of electrical signal amplitude over time. This plot shows a first signal 505 corresponding to the electrical signal generated by acoustic transducer 220 in response to transmitted light beam 230. The plot also shows a later, second signal 510 corresponds to the electrical signal generated by acoustic transducer 220 in response to acoustic waves 410.

Both signals 505 and 510 are the result of directing light beam 225 onto sample 215 for the same given illumination period. As such, plot 500 can be used to extract both the optical attenuation (also referred to as tPA) signal 505 and the photoacoustic (or PA) signal by time-gating plot 500 to distinguish the earlier signal 505 from the later signal 510.

While the description above refers to recording signals 505 and 510 as a continuous time-domain electrical signal, it is contemplated that there can be gaps in this time-domain signal. For example, in some implementations the recording can be paused when the signal level falls below a given threshold. It is also contemplated that signals 505 and 510 can be sampled and recorded, encoded, and/or stored digitally.

Figure 6:
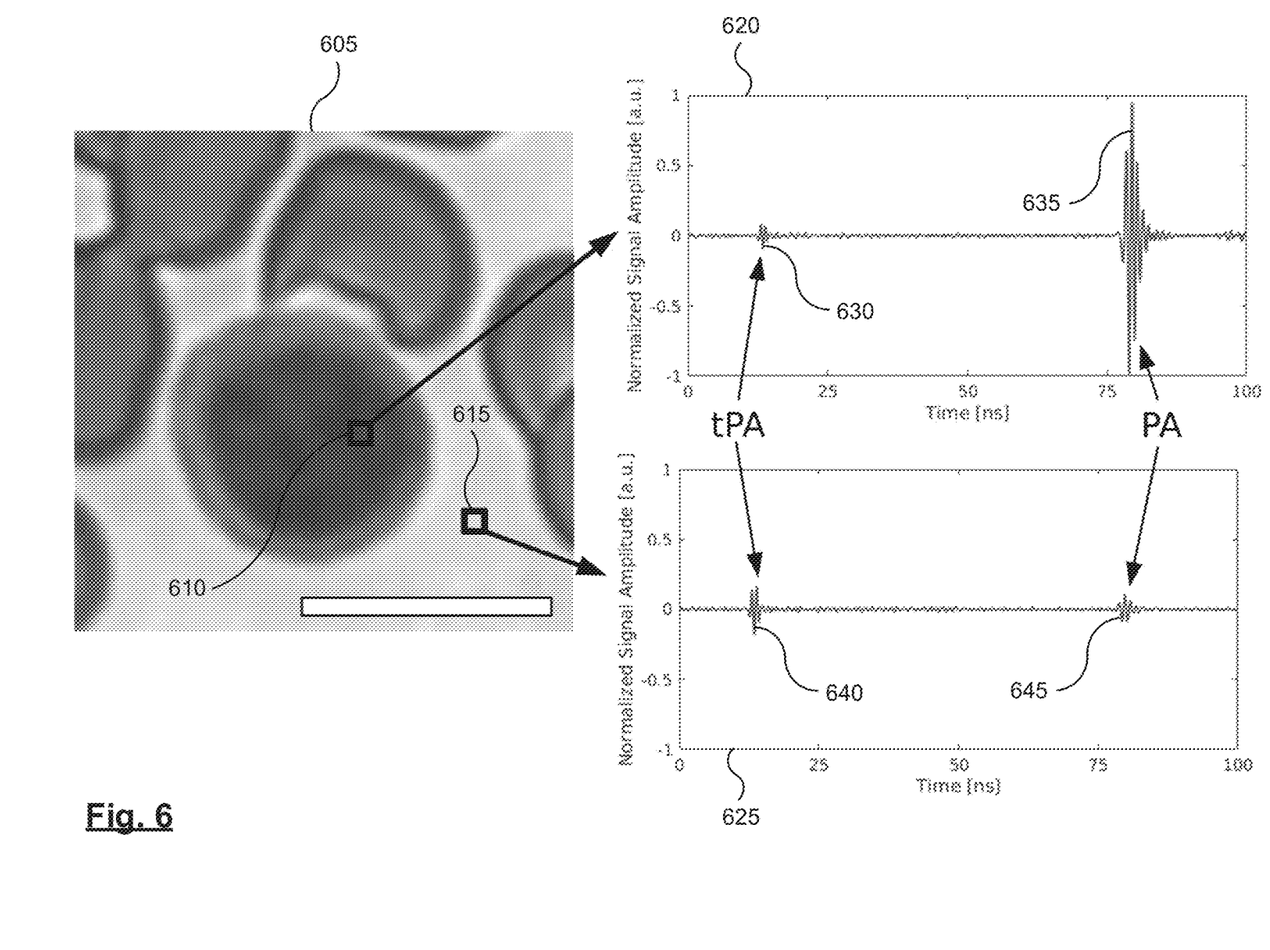
FIG. 6 depicts an image of cells and plots of electrical signal amplitude over time.

Turning now to FIG. 6, an optical micrograph 605 is depicted showing an image of human lymphocyte and red blood cells stained with Wright-Giemsa. The scale bar is 10 µm. In addition, plot 620 shows signal amplitude as a function of time measured in the dual sensing mode and corresponding to region 610 of micrograph 605. Plot 625, in turn, shows signal amplitude as a function of time measured in the dual sensing mode and corresponding to region 615 of micrograph 605. The probing light beam was in the wavelength range of about 532 nm to about 620 nm.

In region 610, there is relatively higher absorption and correspondingly lower transmission of the probe light beam. As relatively little light is transmitted at region 610, the amount of energy in the transmitted light is small and therefore the corresponding tPA signal 630 has a relatively lower amplitude. In contrast, as relatively more optical energy is absorbed by the sample at region 610 (corresponding to the darker color of sample at region 610 in micrograph 605), the sample generates more energetic acoustic waves, which are sensed by the acoustic transducer to produce a photoacoustic (PA) electrical signal 635 of a correspondingly higher amplitude.

In contrast to region 610, at region 615 there is more transmission and less absorption of the probe light. As a result, tPA signal 640, which is based on the energy of the transmitted light, has a larger amplitude compared to the PA signal 645 which is based on the light energy absorbed at region 615. In FIG. 6, for ease of comparison the amplitude of all four signals 630, 635, 640, and 645 is normalized to the amplitude of signal 635.

Figure 7:
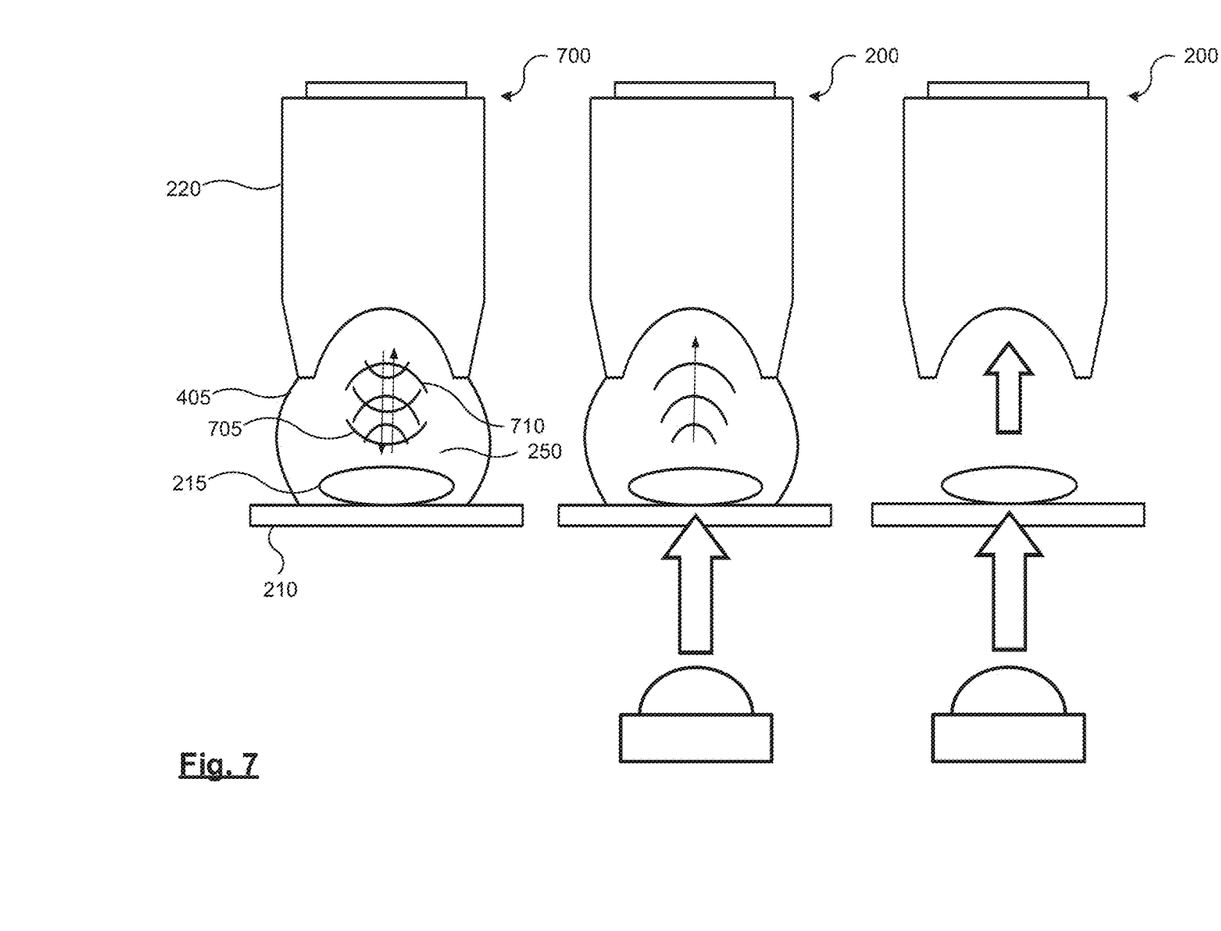
FIG. 7 depicts representations of the apparatus shown in FIGS. 2 and 4 side-by-side with a cross-sectional schematic representation of an apparatus for sensing a sample, according to non-limiting implementations.

FIG. 7 depicts representations of apparatus 200 as shown in FIGS. 2 and 4 side-by-side with a cross-sectional schematic representation of an apparatus 700 for sensing a sample. Apparatus 700 is generally similar to apparatus 200 as shown in FIG. 4, with the main difference being that apparatus 700 need not comprise an optical outlet. In apparatus 700 acoustic transducer 220 generates probe acoustic waves 705 which propagate from acoustic transducer, through coupling medium 405, and towards sample 215. In response to probe acoustic waves 705, echo acoustic waves 710 propagate from sample 215, through coupling medium 405, and towards acoustic transducer 220. Acoustic transducer 220, in turn, can generate an electrical signal based on at least a portion of echo acoustic waves 710.

FIG. 7 shows that if acoustic transducer 220 is used as both a transmitter and receiver of acoustic waves, a subset of the components that are present in apparatus 200 can be used for a yet third mode of imaging, i.e. pulse-echo acoustic imaging.

Figure 8:
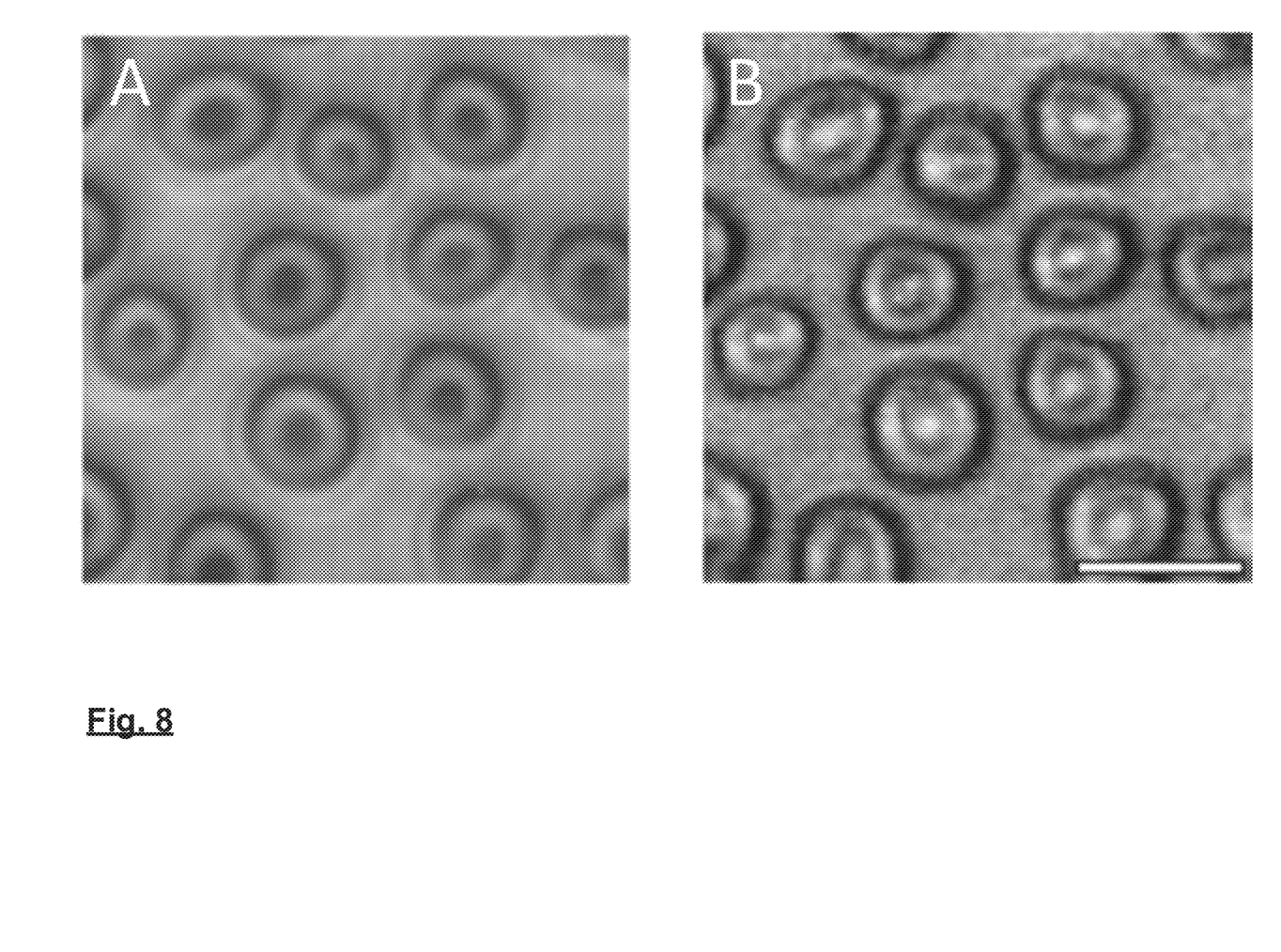
FIG. 8 depicts images of cells.

Turning now to FIG. 8, images A, B are shown. Image A shows an optical micrograph of Wright-Giemsa stained red blood cells in a human blood smear. Image B shows a corresponding tPA image acquired using an air coupling medium. Dark rings are observed around the perimeter and center of the red blood cells. The scale bar is 10 µm.

Image B of FIG. 8 shows that an optical attenuation (or tPA) method, similar to method 100, can be used to form an image of a sample. To form an image of the sample, for each pixel of the image the following steps can be performed: first, a light beam can be directed onto a given area of the sample, where the given area corresponds to the given pixel. The given area of the sample can transmit at least a portion of the light beam to form a transmitted light beam. Next, the transmitted light beam can be received at an acoustic transducer. The acoustic transducer can absorb at least a portion of the transmitted light beam and in response generate an acoustic wave. Subsequently, an electrical signal can be generated at the acoustic transducer. The electrical signal can be generated based on at least a portion of the acoustic wave. Next, a visual characteristic of the given pixel can be determined based on a corresponding characteristic of the electrical signal. In this manner, the light beam can be moved or rastered across the sample to form the multiple pixels that combine to form an image of the sample.

In some implementations, the grey scale intensity of each pixel can be determined based on the corresponding amplitude of the electrical signal at the given area of the sample corresponding to that pixel. In some implementations, the larger the amplitude of the electrical signal corresponding to a given pixel, the lighter will be that pixel on the grey scale.

Figure 9:
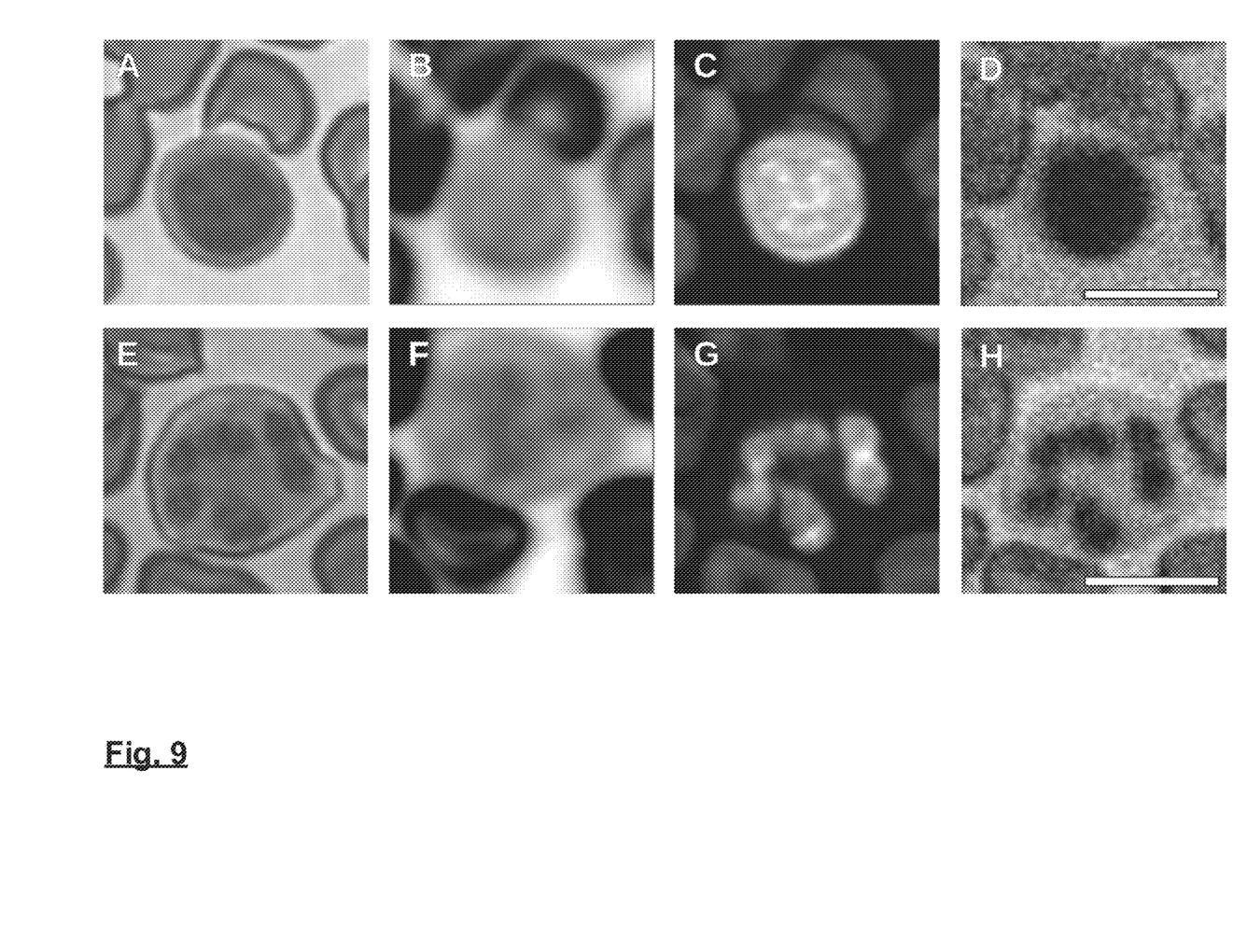
FIG. 9 depicts images of cells.

Referring now to FIG. 9, image A shows an optical micrograph of a human lymphocyte and red blood cells stained with Wright Giemsa. Image B shows an image of the lymphocyte generated using pulse echo ultrasound, which is based on attenuation of sound passing through the sample. Image C shows an image generated with the PA signal gated RF-lines. RF-lines can refer to a record of the amplitude of the electrical signal as a function of time. Image D shows a tPA image corresponding to image C. The tPA image is based on optical attenuation as the imaging light beam passes through the cell. Image E shows an optical micrograph of a human neutrophil and red blood cells. Image F shows an image of the neutrophil generated using pulse echo ultrasound. Image G shows a PA image of the stained neutrophil and surrounding red blood cells. Image H shows a neutrophil tPA image corresponding to image G. In image H, the contour of the cell cytoplasm and surrounding red blood cells can clearly be seen. The scale bars are 10 µm.

In FIG. 9 images G and H were recorded using the dual sensing mode, where for each pixel in these images, following a period of illumination with the light beam, the electrical signal generated by the acoustic transducer was recorded over a period of time. The signal appearing earlier in this record (of electrical signal over time) corresponds to the tPA or optical attenuation signal, and the signal appearing later in the record corresponds to the PA signal. In this manner, the two images can be recorded simultaneously, and distinguished from one another by time-gating the record for each pixel.

Images B and F were recorded using pulse echo ultrasound, where acoustic pulses/waves emitted from the acoustic transducer pass through the cell, reflect from the glass substrate (i.e. the sample holder) and travel back to the acoustic transducer. The electrical signal generated by receiving the acoustic pulses/waves was recorded over time. In these images, the ultrasound measurement was performed after the PA and tPA measurements. However; with appropriate synchronized hardware, all three imaging modalities (a.k.a. sensing modes) can be recorded simultaneously. The tPA signal would be received first, then the PA signal received later, and later further, then ultrasound (US) signal would be received. By appropriate time gating the three images can be created from one measurement acquisition.

As such, and referring to FIGS. 7 and 9, in some implementations the dual sensing mode described above can be extended to a triple sensing mode by performing pulse echo ultrasound sensing/imaging in addition to the photoacoustic and optical attenuation sensing/imaging modes. For example, such a triple sensing mode can comprise the following additional steps: directing a probe acoustic wave generated by the acoustic transducer (e.g. probe acoustic wave 705 shown in FIG. 7) onto the sample. Next, an echo acoustic wave (e.g. echo acoustic wave 710 shown in FIG. 7) can be received at the acoustic transducer. The echo acoustic wave can be generated at least partially by the sample in response to the probe acoustic wave. Subsequently, an additional electrical signal can be generated at the acoustic transducer based on at least a portion of the echo acoustic wave.

In some implementations, the electrical signal output from the acoustic transducer can be recorded as a first (earlier) portion, a second (middle) portion, and a third (later) portion of a continuous time-domain electrical signal. In some implementations, the first, earlier portion can end no later than the start of the second, middle portion, and the second middle portion can end no later than the start of the third, later portion. The first portion can correspond to the optical attenuation (or tPA) signal, the second portion can correspond to the photoacoustic (PA) signal, and the third portion can correspond to the pulse echo ultrasound (US) signal. Time-gating the first, second, and third portions of the continuous time-domain electrical signal can be used to separate/extract the tPA, PA, and US signals.

In the triple sensing mode, the generation and/or timing of the probe and echo acoustic waves associated with the US mode can be timed to avoid overlap and/or interference with the acoustic waves associated with the tPA and PA sensing modes. In some implementations, the probe and echo acoustic waves of the US mode can be timed to occur after/later than the acoustic waves associated with the tPA and PA modes.

Figure 10:
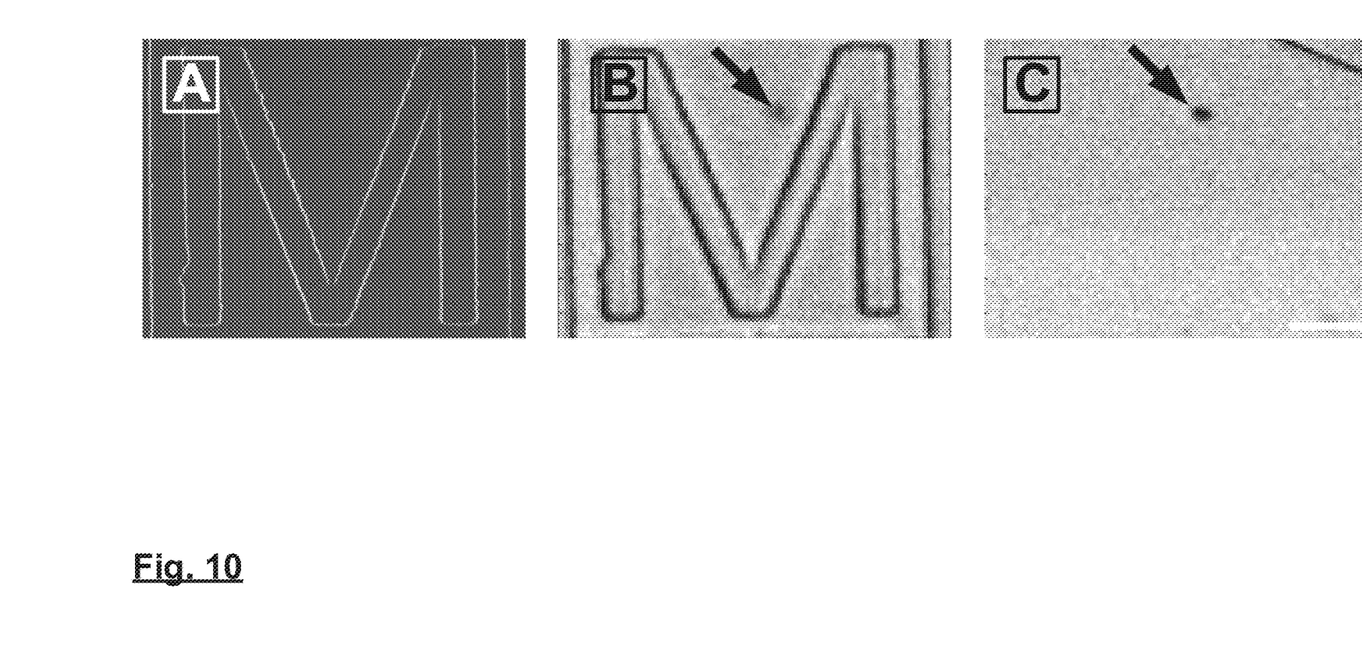
FIG. 10 depicts images of the letter "M" etched into a glass substrate.

Referring now to FIG. 10, images A, B, and C show images of the letter "M" from a grid etched into a glass substrate from a petri dish. Image A shows an optical micrograph taken in transmission mode. Image B shows an optical attenuation image acquired with a 532 nm laser, and no coupling liquid. Image C shows an optical attenuation image with oil as the coupling fluid. The oil matches the index of refraction of the etched glass, and thus no refraction occurs and the M is no longer visible. The dots (marked by arrows in images B and C) in the image are used as fiducial markers. They appear slightly different due to change in focusing.

Figure 11:
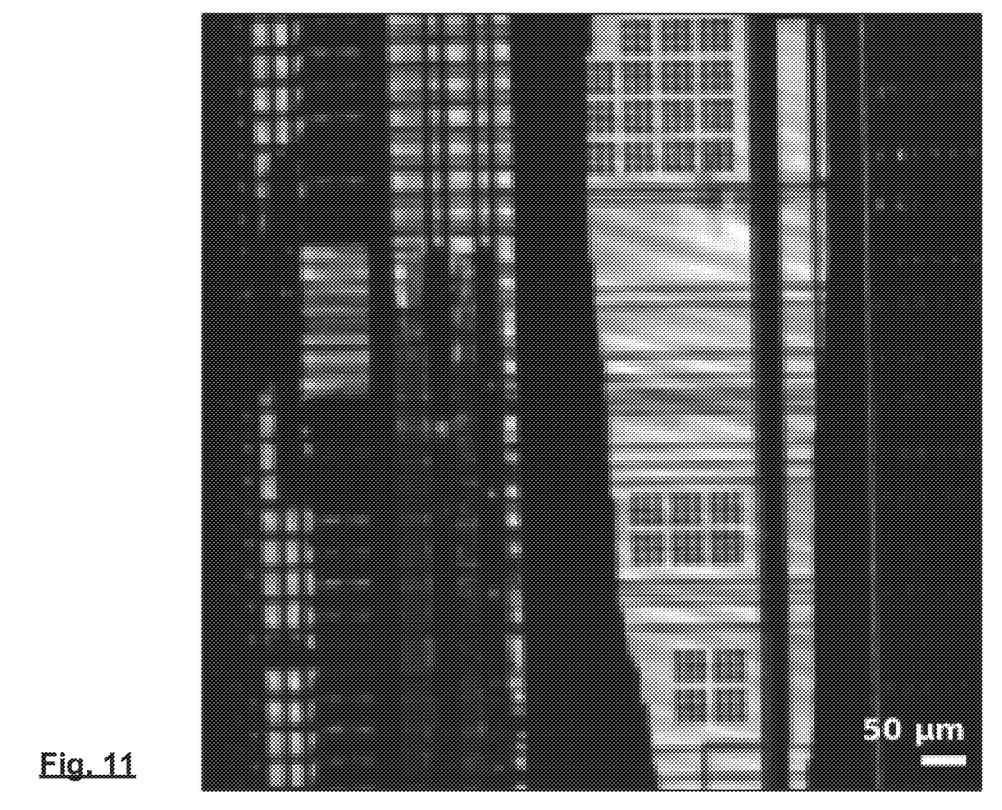
FIG. 11 depicts an image of a processor microchip.

FIG. 11 shows an optical attenuation (or tPA) image of a Texas Instruments TMS320C51 processor microchip taken using a focused 1064 nm laser. The microchip die is opaque in human visible light, and semi-transparent in the infrared. No coupling liquid was used. The resolution is <5 μm. The image demonstrates that the systems and method described herein can be used to create high resolution optical-based images of opaque materials using non-visible light. where features of the microchip are visible.

An exemplary, and non-limiting, implementation of the methods and apparatuses described herein will now be described; see also Michael J. Moore, Eric M. Strohm, and Michael C. Kolios "Simultaneous photoacoustic and optical attenuation imaging of single cells using photoacoustic microscopy", Proc. of SPIE Vol. 9708, 970850 (Mar. 15, 2016), which is incorporated herein by reference in its entirety. In this exemplary implementation, an ultra-high frequency photoacoustic microscope (UHF-PAM) was used to acquire simultaneous conventional PA images and images based on the optical attenuation of the sample.

The ultra-high frequency (UHF) ultrasonic transducers used in acoustic microscopy can have central frequencies and bandwidths in the hundreds of megahertz (MHz). An UHF transducer can comprise a piezoelectric layer of zinc oxide epitaxially grown between two gold electrodes on top of a sapphire buffer rod. In pulse-echo measurements, plane waves generated by the piezoelectric element can propagate through the buffer rod and can be focused to convergent spherical waves by a hemispherical aperture ground into the bottom of the rod. After interaction with the sample, the reflected ultrasound waves can travel through the buffer rod and can be converted to electrical signals by the piezoelectric element. For example, see apparatus 200 shown in FIG. 4.

In transmission mode photoacoustic microscopy (PAM), the microscope optics used to focus the incident laser are opposite the transducer (see FIG. 3). The PA waves emitted by the sample after pulsed laser excitation can follow the same path as reflected ultrasound waves, propagating from the transducer focal zone into the sapphire lens (formed in the buffer rod) before being detected by the piezoelectric element. Photons that are not absorbed or scattered away from the transducer by the sample can fall incident directly upon the sapphire buffer rod. Due to the high optical transmission of sapphire in the visible spectrum these photons can subsequently hit the piezoelectric/electrode element. Since the epitaxially grown zinc oxide in the transducer has negligible absorption in the visible spectrum, the electrodes (or other structures within the transducer) can absorb the photons and generate a PA wave internally within the transducer. PA waves generated in this manner can be colloquially described as tPA signals. These tPA signals can be recorded in the same RF-line as the PA signal emitted by the sample, and can dependent upon both the optical absorption and scattering of photons by the sample.

Sample Preparation

A blood smear was made from a drop of whole human blood extracted via fingerpick from a healthy volunteer in accordance with the Ryerson University Ethics Review Board (REB #2012-210) protocols. The smear was air dried and subsequently fixed by flooding the slide with ice cold methanol and allowing it to completely evaporate. One mL of Wright-Giemsa stain (Sigma Aldrich, USA) was added to the fixed slides, followed by two mL of deionized water after a period of one minute. The stain solution was left to stand at room temperature for 2 minutes before being thoroughly rinsed with deionized water and air dried.

System Setup

A modified scanning acoustic microscope (Kibero GmbH, Germany) equipped with a fiber coupled pulsed 532 nm laser (Teem Photonics, France) was used to image individual cells in the blood smear. The microscope was outfitted with an ultrasound transducer with a central frequency of 1 GHz, and the 532 nm laser had a pulse repetition frequency of 4 kHz and pulse width of 330 ps. The laser beam was directed into the microscope optical path via an optical fiber, focused through a 20× optical objective (Olympus, Japan) and was aligned confocally with the ultrasound transducer on the opposing side of the microscope translation stage. The blood smear was placed on the translation stage and a drop of deionized water was used to provide acoustic coupling between the sample and transducer. The entire system was housed in a temperature controlled enclosure maintained at 37° C. for the duration of the experiment.

Image Acquisition

Target cells were visually identified using the microscope optics and were moved into the laser-transducer confocal spot via the microscope translation stage. After laser irradiation, the resultant PA signals were amplified using a 40 dB amplifier (Miteq, USA) and digitized using a 10 bit digitizer (Agilent, USA) with a sampling frequency of 8 gigasamples per second. All acquired signals were averaged 100 times to increase signal-to-noise ratio (SNR). As illustrated in FIGS. 5 and 6, both the tPA signal and the signal from the target cell were captured in the acquired RF-lines. The cells were scanned in a raster pattern with a step size of 0.33 μm. After scanning, the acquired RF lines were time gated to contain only the tPA signal or the PA signal from the sample. Two Maximum Amplitude Projection (MAP) images were produced from these time gated regions by assigning each scan position a gray scale value with intensity proportional to the maximum amplitude of the RF-line acquired at that coordinate.

Air-Coupled Measurements

To test whether the tPA signals were produced within the transducer, raster scans were performed without the use of any liquid coupling medium. In this case, no detectable photoacoustic waves generated at the sample can propagate to the buffer rod due to a combination of the high attenuation coefficient and low acoustic impedance of air (i.e. high impedance mismatch between air and the sample), and only photons which hit the transducer directly can contribute to the tPA signal. A tPA image of stained red blood cells scanned using this setup is shown in FIG. 8, image D. The red blood cells in the tPA image exhibit two dark rings: one around the cell perimeter, and the other in the center of the cell. Both the perimeter and concave center of the red blood cell have high curvature, and so these dark regions can be caused by scattering of the tightly focused laser beam away from the transducer element due to the curved red blood cell surface and the difference in the refractive index of the red blood cell and air.

Stained Cells

Representative RF-lines from a Wright-Giemsa stained blood smear are shown in plots 620 and 625 of FIG. 6. When a strongly stained area (e.g. the cell nucleus/region 610) was measured, the PA signal from the sample was approximately 10 fold larger than that of the tPA signal. Conversely, in areas with scant stain uptake or with residual dye persisting on the glass substrate after the rinsing process (e.g. region 615), the tPA signal was stronger.

Optical images of a stained lymphocyte and a stained neutrophil are shown in FIG. 9 images A and D, respectively. Dark staining is observed in the nuclei, while lighter shades are present in the cell cytoplasm of the lymphocyte and neutrophil, respectively. The PA images from the segment of the RF-line time gated to contain only the PA signal from the sample are shown in FIG. 9, images B and E. Strong PA signals were observed from the nuclei, with weaker amplitude signals from the surrounding red blood cells. In the scan of the lymphocyte, there was considerable PA signal from the cell cytoplasm; however, in the neutrophil the PA signal from the cytoplasm was low.

FIG. 9 images C and F were created with the tPA time gated data. Dark regions in both tPA MAP images corresponded to regions of strong optical attenuation. Since the tPA images are based on optical scattering and absorption, this technique can show additional detail that may not be observed in the PA images alone. For example, in FIG. 9 image F, the boundary of the neutrophil cytoplasm is clearly delineated, while it is difficult to see the same in the corresponding PA image E. Additionally, the boundary of the red blood cells in FIG. 9 images C and F can be visually discerned.

FIGS. 8 and 9 can demonstrate that the tPA images exhibit unique features that may not be visible in pure PA images. The accentuation of features in the tPA images, especially in areas of high curvature, can be helpful in visualizing weakly absorbing cells which produce very weak to negligible PA signals. Additionally, because the tPA signals can be acquired without the use of an acoustic coupling medium, i.e. when there is an acoustic gap between the sample and the acoustic transducer, this technique can be useful for examining samples which cannot be submerged in water or other liquids.

The methods and apparatuses described herein can have application in various areas including, but not limited to, measurement of sample optical absorption as a function of wavelength; imaging using non human-visible light; high resolution imaging of features at depth in a sample such as microchips and cells; index of refraction determination; measurements of sample optical attenuation properties; thin film analysis; non-destructive testing and characterization; and the like.

The above-described implementations of the invention are intended to be examples of the present invention and alterations and modifications may be effected thereto, by those of skill in the art, without departing from the scope of the invention which is defined solely by the claims appended hereto.

We claim:

1. A method for sensing a sample, the method comprising:
   directing a light beam onto the sample, the light beam being at least partially transmittable through sample to form the transmitted light beam;
   receiving the transmitted light beam at an acoustic transducer, the acoustic transducer absorbing at least a portion of the transmitted light beam and in response generating an acoustic wave; and
   generating an electrical signal at a piezoelectric element of the acoustic transducer, the electrical signal generated based on at least a portion of the acoustic wave.

2. The method of claim 1, wherein the sample is separated from the acoustic transducer by an acoustic gap.

3. The method of claim 2, wherein the acoustic gap is an air gap.

4. The method of claim 1, wherein the piezoelectric element generates the acoustic wave based on the photoacoustic effect.

5. The method of claim 1, wherein the acoustic transducer comprises an ultrasound transducer.

6. The method of claim 5, wherein the ultrasound transducer has a central frequency in a range of about 100 MHz to about 1000 MHz.

7. The method of claim 1, wherein the acoustic transducer comprises:
   a buffer member configured to conduct the acoustic wave; and
   the piezoelectric element acoustically coupled to the buffer member, the piezoelectric element configured to generate the electrical signal based on the acoustic wave.

8. The method of claim 1, wherein the light beam comprises a pulsed laser beam.

9. The method of claim 1, wherein the light beam is focused at one of:
   a first point underneath a surface of the sample, the first point being inside the sample; and
   a second point at the surface of the sample.

10. The method of claim 1, further comprising:
    after the receiving the transmitted light beam at the acoustic transducer, receiving at the acoustic transducer at least a portion of a further acoustic wave, the further acoustic wave generated by the sample absorbing at least a further portion of the light beam and in response generating the further acoustic wave; and
    generating a further electrical signal at the piezoelectric element of the acoustic transducer, the further electrical signal generated based on at least a portion of the further acoustic wave.

11. The method of claim 10, wherein the sample generates the further acoustic wave based on the photoacoustic effect.

12. The method of claim 10, further comprising:
    recording the electrical signal and the further electrical signal respectively as a first portion and a second portion of a continuous time-domain electrical signal, the first portion ending no later than a start of the second portion.

13. The method of claim 10, further comprising:
    directing a probe acoustic wave onto the sample, the probe acoustic wave generated at the acoustic transducer;
    receiving at the acoustic transducer an echo acoustic wave, the echo acoustic wave generated at least partially by the sample in response to the probe acoustic wave; and
    generating an additional electrical signal at the piezoelectric element of the acoustic transducer, the additional electrical signal generated based on at least a portion of the echo acoustic wave.

14. The method of claim 13, further comprising:
    recording the electrical signal, the further electrical signal, and the additional electrical signal respectively as a first portion, a second portion, and a third portion of a continuous time-domain electrical signal, the first portion ending no later than a start of the second portion, and the second portion ending no later than a corresponding start of the third portion.

15. A method of forming an image of a sample, the image having a plurality of pixels, the method comprising:
    for each given pixel of the image:
    directing a light beam onto a given area of the sample, the given area corresponding to the given pixel, the given area of the sample transmitting at least a portion of the light beam to form a transmitted light beam;

receiving the transmitted light beam at an acoustic transducer, the acoustic transducer absorbing at least a portion of the transmitted light beam and in response generating an acoustic wave;

generating an electrical signal at a piezoelectric element of the acoustic transducer, the electrical signal generated based on at least a portion of the acoustic wave; and determining a visual characteristic of the given pixel based on a corresponding characteristic of the electrical signal.

16. The method of claim 15, wherein the visual characteristic comprises a grey scale intensity and the corresponding characteristic of the electrical signal comprises an amplitude of the electrical signal.

17. The method of claim 15, wherein the sample is separated from the acoustic transducer by an acoustic gap.

18. An apparatus for sensing a sample, the apparatus comprising:

an optical outlet configured to direct a light beam onto the sample, at least a portion of the light beam being transmittable through the sample to form a transmitted light beam;

an acoustic transducer having a piezoelectric element, the acoustic transducer positioned to receive the transmitted light beam, the acoustic transducer configured to:

absorb at least a portion of the transmitted light beam and in response generate an acoustic wave; and generate, at the piezoelectric element, an electrical signal based on at least a portion of the acoustic wave; and a sample holder disposed between the optical outlet and the acoustic transducer, the sample holder configured to support the sample in a path of the light beam.

19. The apparatus of claim 18, wherein the acoustic transducer comprises:

a buffer member proximate the sample holder, the buffer member configured to conduct the acoustic wave; and the piezoelectric element distal from the sample holder, the piezoelectric element acoustically coupled to the buffer member, the piezoelectric element configured to generate the electrical signal based on the acoustic wave.

20. The apparatus of claim 19, wherein:

the optical outlet comprises a lens having an optical focal point;

the buffer member is shaped to have an acoustic focal point; and the lens and the buffer member are positioned such that the optical focal point about coincides with the acoustic focal point.

\* \* \* \* \*